United States Patent
Luther

(10) Patent No.: US 7,706,590 B2
(45) Date of Patent: Apr. 27, 2010

(54) METHOD AND DEVICE FOR INTERROGATING SAMPLES USING LASER SCANNING CYTOMETRY AND OTHER TECHNIQUES

(75) Inventor: Edgar A. Luther, Wilmington, MA (US)

(73) Assignee: CompuCyte Corporation, Westwood, MA (US)

(*) Notice: Subject to any disclaimer, the term of this patent is extended or adjusted under 35 U.S.C. 154(b) by 408 days.

(21) Appl. No.: 11/040,183

(22) Filed: Jan. 21, 2005

(65) Prior Publication Data
US 2005/0190365 A1    Sep. 1, 2005

Related U.S. Application Data

(60) Provisional application No. 60/539,631, filed on Jan. 28, 2004.

(51) Int. Cl.
*G06K 9/28* (2006.01)
*G02B 21/08* (2006.01)

(52) U.S. Cl. .......................... 382/133; 382/134; 356/338

(58) Field of Classification Search .................. 382/128, 382/133–134; 356/72–73, 36, 39, 129, 317, 356/318, 336–338; 435/4, 7.24, 29, 325; 436/63, 164, 172; 702/19, 21
See application file for complete search history.

(56) References Cited

U.S. PATENT DOCUMENTS

| | | | |
|---|---|---|---|
| 4,202,625 A | 5/1980 | Weiner et al. .................. 355/52 |
| 4,284,412 A | 8/1981 | Hansen et al. .............. 435/7.24 |
| 4,325,706 A | 4/1982 | Gershman et al. .............. 435/6 |
| 4,647,531 A | 3/1987 | Kamentsky .................. 435/7.24 |
| 5,072,382 A | 12/1991 | Kamentsky .................. 382/133 |
| 5,093,866 A * | 3/1992 | Douglas-Hamilton et al. .... 382/133 |
| 5,523,207 A | 6/1996 | Kamentsky et al. ............. 435/6 |
| 5,561,556 A | 10/1996 | Weissman .................... 359/396 |
| 5,587,833 A | 12/1996 | Kamentsky .................. 359/393 |
| 5,602,674 A * | 2/1997 | Weissman et al. ........... 359/393 |
| 5,633,945 A | 5/1997 | Kamentsky .................. 382/129 |
| 5,721,435 A * | 2/1998 | Troll ...................... 250/559.29 |
| 5,885,840 A | 3/1999 | Kamentsky et al. ........... 436/63 |
| 6,002,788 A | 12/1999 | Luther ........................ 382/133 |
| 6,372,895 B1 * | 4/2002 | Bentsen et al. ............... 536/4.1 |
| 6,400,453 B1 * | 6/2002 | Hansen ..................... 356/237.1 |
| 2002/0176069 A1 * | 11/2002 | Hansen et al. ................. 356/73 |

FOREIGN PATENT DOCUMENTS

WO    WO 03/016875    *    2/2003

* cited by examiner

*Primary Examiner*—Brian Q Le
(74) *Attorney, Agent, or Firm*—Sunstein Kann Murphy & Timbers LLP

(57) ABSTRACT

A method of using laser scanning cytometry to provide a viewable image of a specimen includes impinging a beam of light from a light source on the specimen and positioning a detector such that the detector captures only a portion of an unimpinged beam from the light source, and the detector captures forward scattered light from the beam after the beam impinges the specimen. Forward scattered light from the beam is captured with the detector after the beam impinges the specimen to produce an image of the specimen, and the position of the detector is adjusted to control the contrast of the image.

18 Claims, 9 Drawing Sheets

Image of calibration beads in the shaded relief mode.

58 micron

Pixel intensity profile going through a single bead.

Adjust (Scan View) window set to shaded relief mode.

Image of calibration beads in the light loss mode.

58 micron

Pixel intensity profile going through a single bead.

Adjust (Scan View) window set to light loss mode.

ID AND DEVICE FOR
INTERROGATING SAMPLES USING LASER
SCANNING CYTOMETRY AND OTHER
TECHNIQUES

The present application claims priority from U.S. Provisional Application No. 60/539,631, filed Jan. 28, 2004, which is hereby incorporated herein by reference.

TECHNICAL FIELD

The present invention relates to detecting light interaction with microscopic specimens, and particularly to imaging of cells due to one, or a combination, of light scattering and light extinction from light absorption, negative scatter, or refraction.

BACKGROUND ART

Laser scanning cytometry ("LSC") is a well established analysis tool that can be used to determine various characteristics of cells. U.S. Pat. No. 4,647,531, hereby incorporated herein by reference, provides a generalized cytometry instrument which includes translocating means which provides electromechanical forces capable of moving a surface upon which live cells are immobilized. The translocating means may alternatively move a cell locating means, illuminating means and detecting means over a stationary surface to produce a representation or graphical illustration of cell numbers and responses.

Some LSC systems utilize a blocker bar configured to prevent a beam of light from striking a detector when a cell is not present between the source of the beam and the detector. Such a configuration, however, allows forward scattered light to strike the detector when the beam strikes a cell before impinging on the blocker bar. The capture of forward scattered light by the detector enables the creation of a dark field image with an undefined bright field representing the cells (i.e., contrast-field image).

U.S. Pat. No. 6,002,788 ('788 patent), also hereby incorporated by reference herein, provides a method and device for creating visual images of cells using LSC by modifying a blocker bar to be configured such that a portion of a beam of light strikes a detector when a cell is not present between the source of the beam and the detector. When the beam impinges on a cell, however, a portion of the forward scattered light impinges on the detector creating an additional signal while another portion of the forward scattered light is negatively scattered. The contrast of detected scattered light permits the detector to create signals capable of creating a visual image of the cell.

The use of a blocker bar in LSC requires the manipulation of an additional element that complicates the design of such devices. In addition, a blocker bar may require specific manufacturing to optimize visual imaging, as taught by the '788 patent, or the contrast-field imaging presented in earlier LSC devices. Thus, an advantage may be accrued by eliminating the use of a blocker bar.

SUMMARY OF THE INVENTION

Embodiments of the invention allow the interrogation of a sample without the use of a blocker bar to modify an electromagnetic beam that is captured by a detector to produce an visual image of the sample.

In one embodiment of the invention there is provided a system for visually imaging a sample. The system includes a source of laser light for creating a scanning beam of light, a movable sample support for supporting a sample, and a movable detector. The movable sample support and the scanning beam are moved relative to one another such that a portion of the sample support is scanned by the beam. The beam is only attenuated substantially by the sample support and its contents before impinging on the detector. The detector is configured to detect only a portion of the beam when a sample is not impinged by the beam, and to detect only a portion of forward scattered light from the sample when the sample is impinged by the beam. Such a system may be utilized with a laser scanning cytometer. The detector may be variably positioned for altering the contrast of a visual image produced by the system.

In another embodiment of the invention there is provided a system for creating a contrast-field image of a sample. The system includes a source of laser light for creating a scanning beam of light, a movable sample support for supporting a sample, and a movable detector. The movable sample support and the scanning beam are moved relative to one another such that a portion of the sample support is scanned by the beam. The beam is only attenuated substantially by the sample support and its contents before impinging on the detector. The detector is configured to detect the beam when a sample is not impinged by the beam, and to detect a light loss of the beam when the sample is impinged by the beam. Again, such a system may be utilized with a laser scanning cytometer. The detector may be variably positioned for altering the contrast of a contrast-field image produced by the system.

Another embodiment of the invention is directed toward a system that may create visual images or the contrast-field images of the previously described embodiments. In such an embodiment, the detector may be variably positioned and configured to practice either embodiment.

In accordance with a further embodiment of the invention, a method of using laser scanning cytometry to provide a viewable image of a specimen includes impinging a beam of light from a light source on the specimen and positioning a detector such that the detector captures only a portion of an unimpinged beam from the light source, and the detector captures forward scattered light from the beam after the beam impinges the specimen. Forward scattered light from the beam is captured with the detector after the beam impinges the specimen to produce an image of the specimen, and the position of the detector is adjusted to control the contrast of the image.

In accordance with another embodiment of the invention, an apparatus for producing an image of a specimen includes a light source capable of producing a beam of light and a detector. The detector is configured to capture a portion of the beam when the beam is uninterrupted, and is further configured to capture forward scattered light when the beam impinges on the specimen, which is used to produce an image of the specimen. In accordance with a related embodiment, the detector may be further configured to capture the entire beam of light when the beam is uninterrupted.

In accordance with yet a further embodiment of the invention, an apparatus for producing an image of a specimen includes a light source capable of producing a beam of light and a detector. The detector is repositioned with respect to the beam of light and is configured to produce a signal of a first intensity when the beam is uninterrupted and configured produce a signal of a second intensity when forward scattered light impinges on the specimen. The signals are used to produce a visual image of the specimen.

In accordance with related embodiment, the light source may be a monochromatic light source. In accordance with other related embodiments, the detector may be configured to produce a signal of a third intensity when light is refracted by the specimen and/or the detector may be configured to produce a signal of a fourth intensity when light is converted to fluorescence by the specimen.

In accordance with another embodiment of the invention, a method for producing an image of a specimen includes producing a beam of light and adjusting the position of a detector such that only a portion of an unimpinged beam from the light source is detected to producing a signal of a first intensity. The position the detector is also adjusted such that light scattered by the specimen is detected to produce a signal of a second intensity; and the signals are used to form an visual image of the specimen.

In accordance with related embodiments, adjusting the position of the detector such that light scattered by the specimen is detected may include adjusting the position of the detector such that forward scattered light is detected. In accordance with other related embodiments, the method may include positioning the detector such that light refracted by the specimen is detected and a signal of a third intensity is produced. The method may also include positioning the detector such that light converted to fluorescence is detected and producing a signal of a fourth intensity. Further producing a beam of light may include producing a beam of monochromatic light and/or producing a beam of light may include using laser scanning cytometry.

BRIEF DESCRIPTION OF THE DRAWINGS

The foregoing features of the invention will be more readily understood by reference to the following detailed description, taken with reference to the accompanying drawings, in which.

DETAILED DESCRIPTION OF THE SPECIFIC EMBODIMENTS

Embodiments of the present invention are directed toward interrogating samples with a source producing an electromagnetic beam and detecting the interaction of such a beam with the sample. Furthermore, some embodiments of the invention may have particular relevance when applied to laser scanning cytometry ("LSC"). As such, some of the embodiments described herein may utilize the context of LSC. However, embodiments of the invention are not necessarily limited to the typical operating parameters of LSC. Samples to be interrogated may be cells or other materials, such as particles with a pore. Also, the sources of laser light that may be used in some embodiments are not necessarily limited to visible light, but can include other wavelengths including those in the UV and IR range. As well, the embodiments may be suitable for detecting samples in other light detection arrangements besides LSC.

Figure 1A:
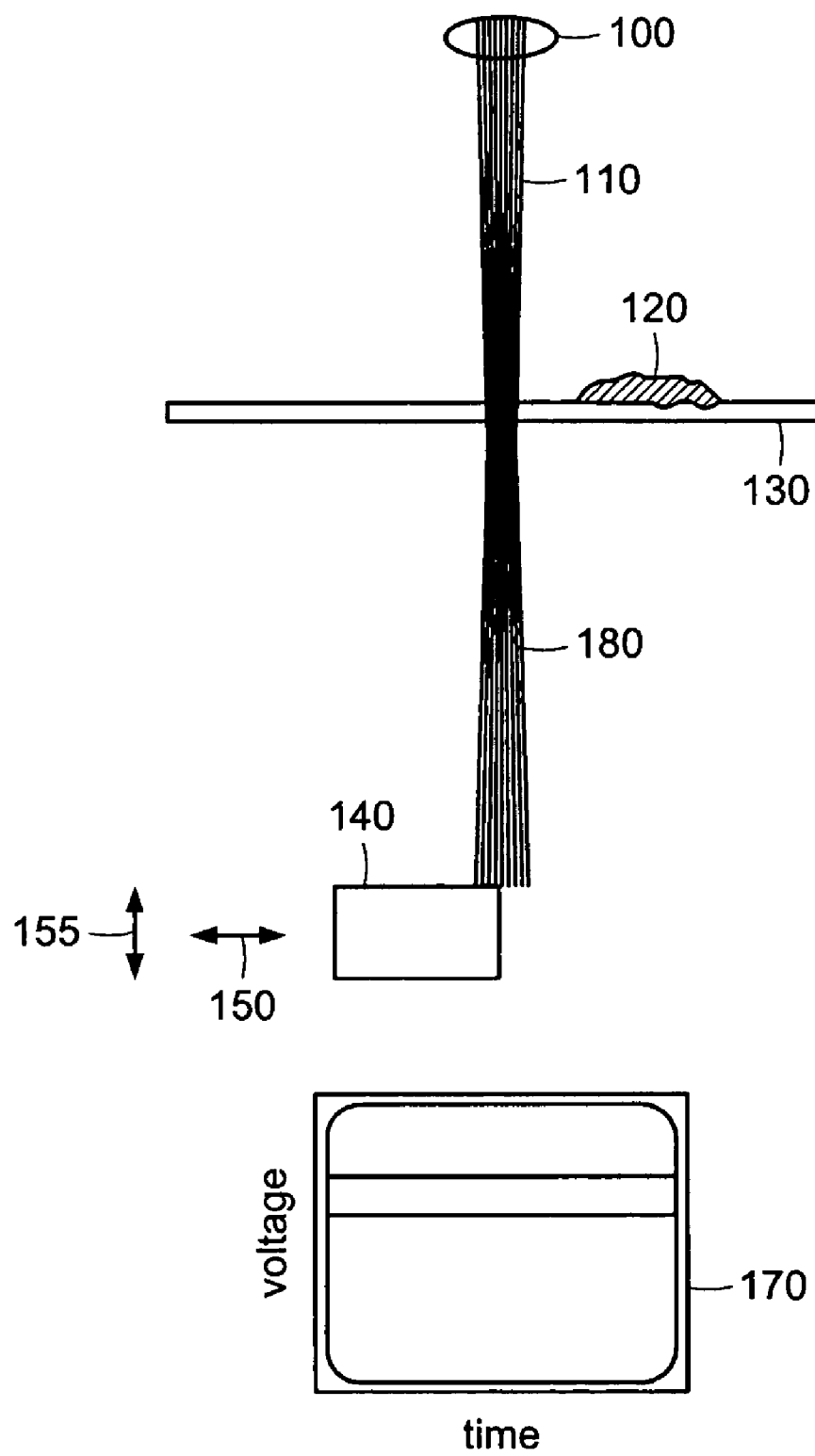
FIG. 1A depicts an embodiment of the invention used to create a visual image of a sample when a beam of light does not impinge a sample.
Figure 1B:
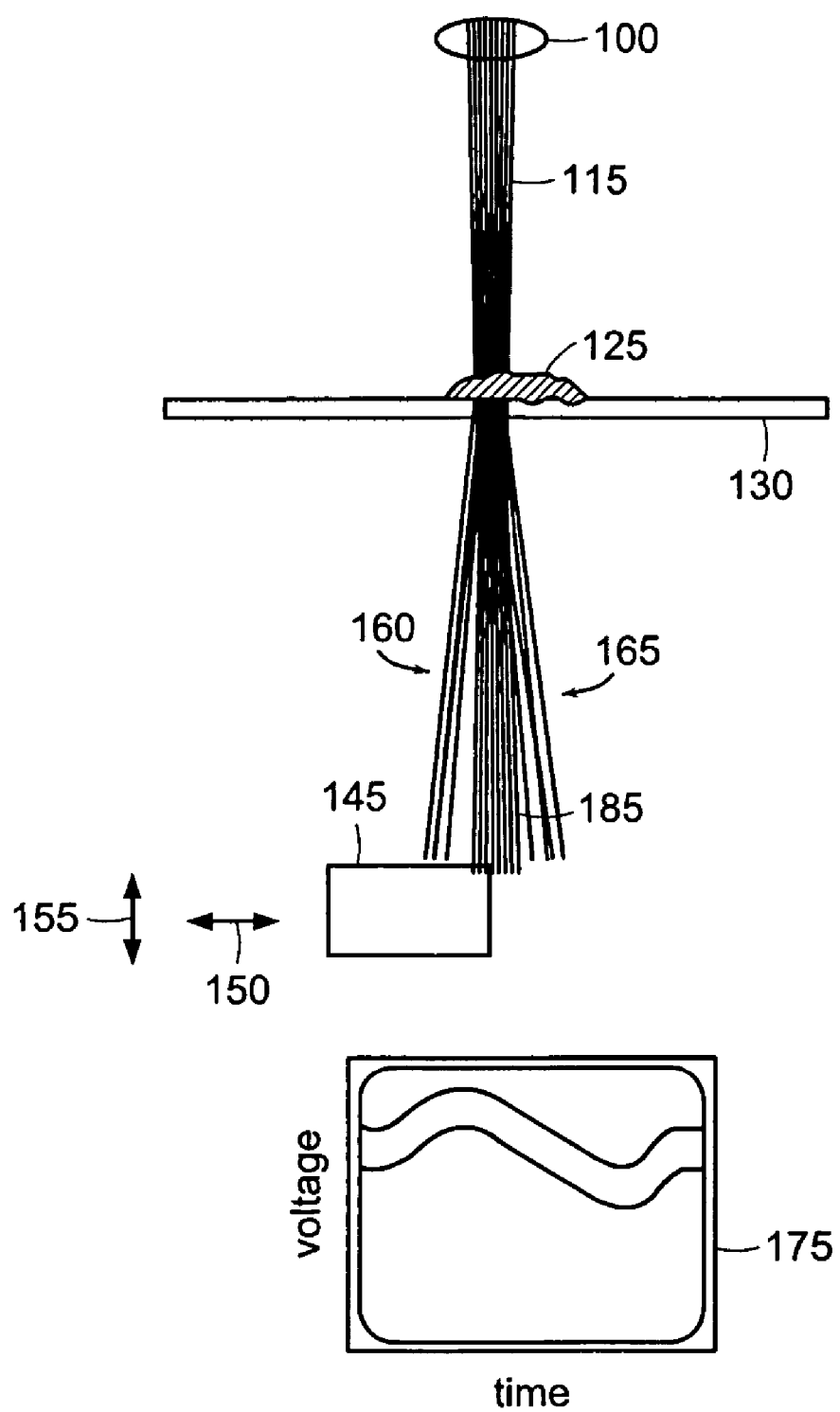
FIG. 1B depicts an embodiment of the invention used to create a visual image of a sample when a beam of light impinges a sample.

FIGS. 1A and 1B depict features of one embodiment of the invention. As shown in FIG. 1A, a source 100 creates a laser beam of light 110. A detector 140 is used to detect light and create a signal. The embodiment of FIGS. 1A and 1B may be incorporated into a device to conduct LSC. Using LSC, a slide 130 (or other sample support) supports one or more samples 120 (e.g., cells) to be imaged. The slide 130 is impinged by the beam 110, and allows transmission of the beam. When the beam 115 strikes a sample 125 to be interrogated, however, the beam 115 may be attenuated by a number of mechanisms (e.g., scattering, absorption, and refraction). The beam 110 is scanned back and forth in a direction perpendicular to the plane of FIG. 1A. The slide 130 may be moved in a direction perpendicular to the direction 150 of the scanning beam. Thus, a raster scan of the slide 130 may be obtained by coordinating the movement of the beam 110 and slide 130 (i.e., scanning the slide). As known to those skilled in the art, various other means may be used for scanning a portion of the slide by inducing relative motion between the beam 110 and the slide 130.

The detector 140 may be adjustably positioned in various directions 150, 155. The detector 140 (e.g., a photodiode) may create a voltage signal correlating with the amount of light impinging on the detector 140 at a particular moment. Further, as is known in the art the detector may include or be coupled to an amplifier. As the slide 130 is scanned, the voltage signal produced by the detector 140 may change as a function of time depending upon whether anything on the slide 130 attenuates the beam 110 reaching the slide 130. For example, the graph of voltage as a function of time 170 associated with FIG. 1A shows that a constant voltage is measured by the detector 140 as light strikes the detector as long as the scanning process does not impinge upon a sample 120 on the slide 130.

In the embodiment of FIGS. 1A and 1B, the beam is only attenuated substantially by the slide and any sample or other contents supported by the slide between the beam's emission at the source and the beam's disposition before impinging upon the detector. The detector 140 is configured such that when the beam 110 impinges upon a location of the slide 130 that does not support a sample 120, only a portion of the beam 180 transmitted through the slide 130 impinges on the detector 140; the remaining portion of the beam 180 does not impinge on the detector 140. This configuration may be achieved, for example, by positioning the detector 140 to have asymmetric exposure to the impinging beam in the absence of a sample, as depicted in FIG. 1A.

Figure 1C:
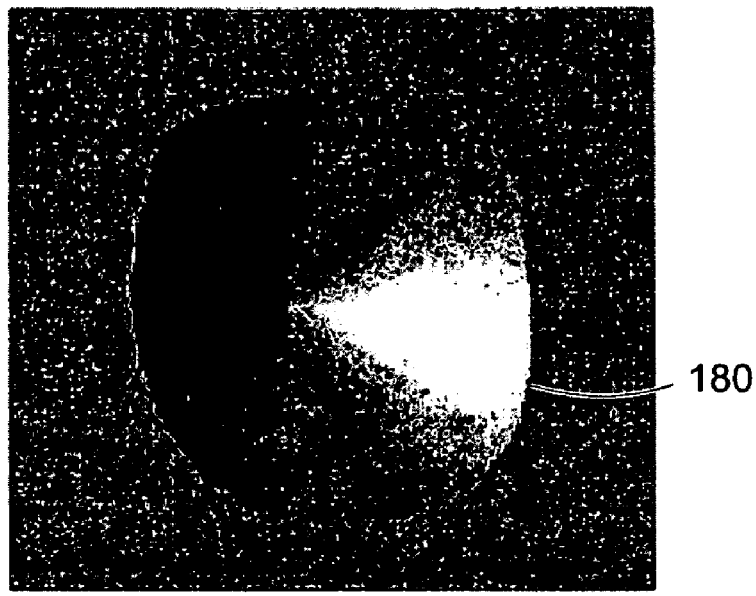
FIG. 1C depicts a visual image created by the embodiment of the invention exemplified by FIGS. 1A and 1B.

Furthermore, as shown in FIG. 1B, the configuration of the detector 145 is such that when a sample 125 is impinged by the beam 115 a portion of the forward scattered light 160 impinges on the detector 145. The configuration, however, also causes a portion of the forward scattered light (and in some cases, both the scattered and refracted light) 165 to miss the detector 145. The contrast in detection of forwarded scattered light and other portions of the beam results in a detector 145 being capable of producing a voltage versus time plot 175 that exhibits pronounced voltage fluctuations as slide 130 is scanned. The voltage signals may be translated into a visual image 180, as shown in FIG. 1C by registering each voltage signal with the corresponding specific position of the slide that is impinged by the beam 115. The detector may be positioned to alter the amount of forward scattered light captured by the detector, or the amount of other components of the transmitted beam, in order to alter the contrast of the visual image formed.

In accordance with embodiments of the invention, movement of the beam 110, the slide 130, and the detector 140 is accomplished under compute software control well know in the art. Further, the assembly holding the detector 140 (or the detector itself) may be coupled to a stepping motor (or other mechanism capable of producing drive power) and movement of the stepping motor may also be controlled by computer software resident in a cytometer data acquisition module. Such a module may define different modes of operation. For example, a "shaded relief" mode of operation may correspond to the optical configuration of FIGS. 1A-1B and a "light loss" mode (which will be explained in greater detail below) may correspond to the optical configuration of FIGS. 2A-2B.

Figure 5:
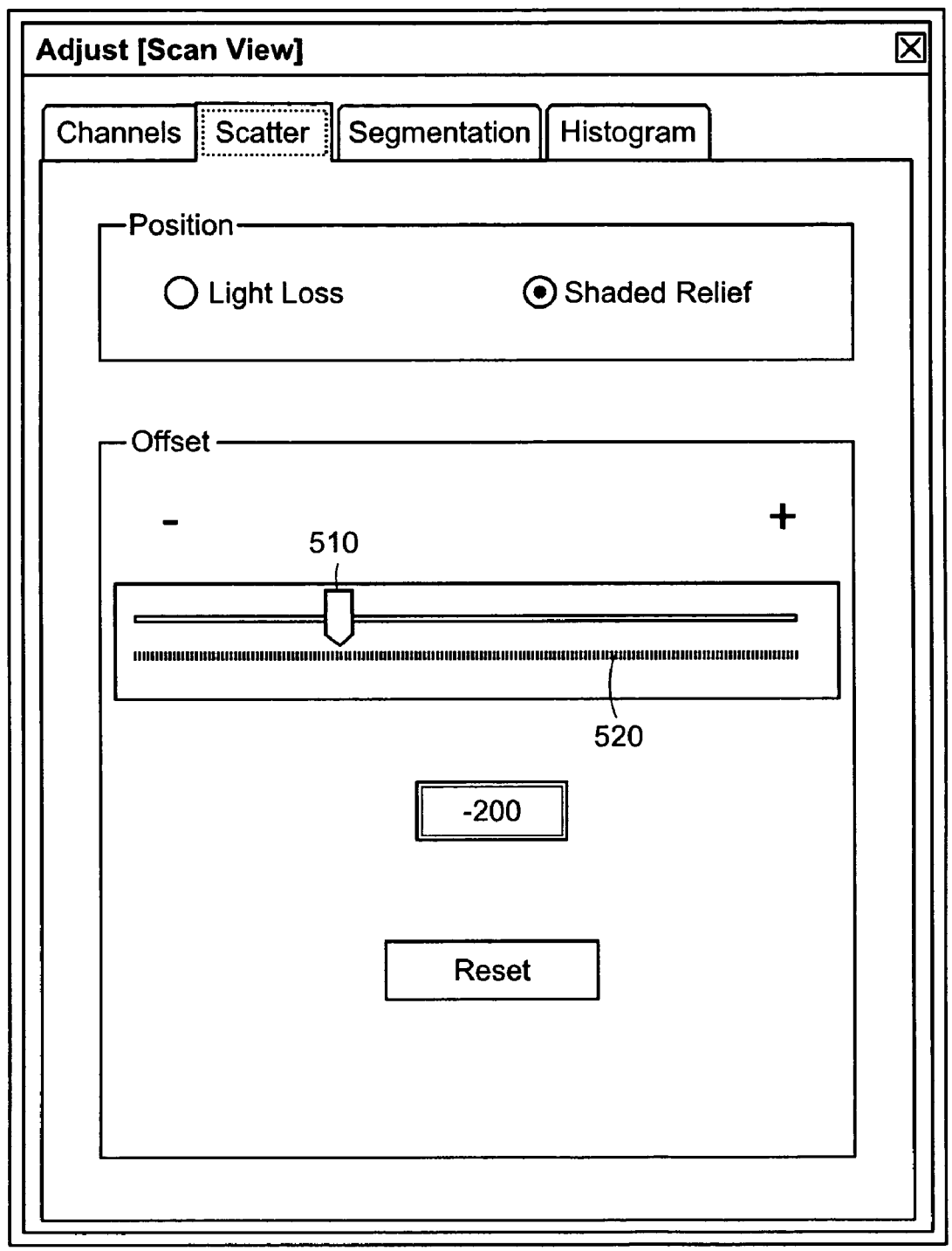
FIG. 5 depicts a graphical user interface which may be used to view an image in a shaded relief mode generated in accordance with the embodiments of FIGS. 1A-1B.

As described above, the shaded relief mode allows movement of the detector in relation to the geographical location of the interrogating laser beam. The detector 140 may be positioned by appropriate mechanisms as known to those skilled in the art. For example, the detector may be adjustably positioned via a graphical user interface such as that shown in FIG. 5. Movement of the slider bar 510 using a computer mouse results in a corresponding movement of the detector 140. The center of the scale 520 (the "zero position") is defined as the calibration point where the unobstructed signal is 50% attenuated. The amount of movement changes the position of the detector relative to the calibrated zero position. Negative offsets translate to increased angles of light scatter begin measured, and thus increased shaded relief effect. Positive offsets result in less shaded relief effect.

Figure 3:
FIG. 3 depicts a visual image of calibration beads generated in accordance with the embodiment of the FIGS. 1A-1B.
Figure 4:
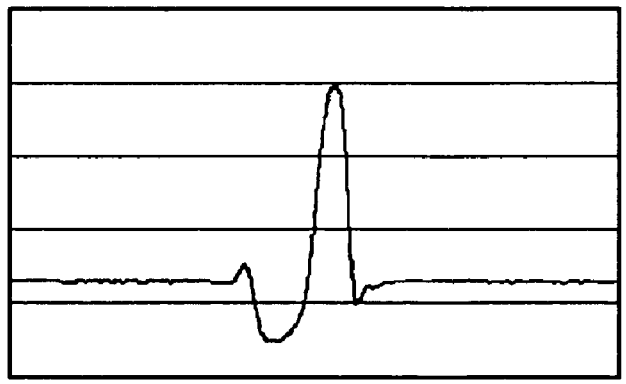
FIG. 4 depicts and graphical illustration of a pixel intensity profile through a bead of FIG. 3.

FIG. 3 depicts a demonstration of the shaded relief mode wherein a portion of a microscope slide containing 10 micron calibration particles was scanned. A pixel intensity profile that was obtained for a line going through a single bead is depicted in FIG. 4.

Thus the embodiment of the invention depicted in FIGS. 1A and 1B enables the imaging of samples without the use of a blocker bar. The configuration of the detector in such an embodiment includes positioning, orienting, and sizing the detector to allow the capture of light as required by the embodiment. Other configurations besides the one depicted in FIGS. 1A and 1B may be readily developed by those skilled in the art. For example, though FIGS. 1A and 1B may show beams that are unobstructed, except for impingement on the slide, mirrors may be used to manipulate the beams to configure a system in a particular manner.

Figure 2C:
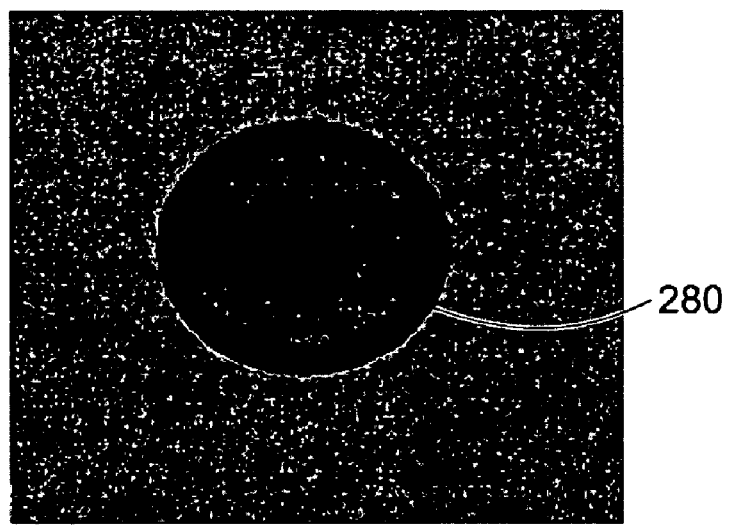
FIG. 2C depicts a contrast-field image created by the embodiment of the invention exemplified by FIGS. 2A and 2B.
Figure 2A:
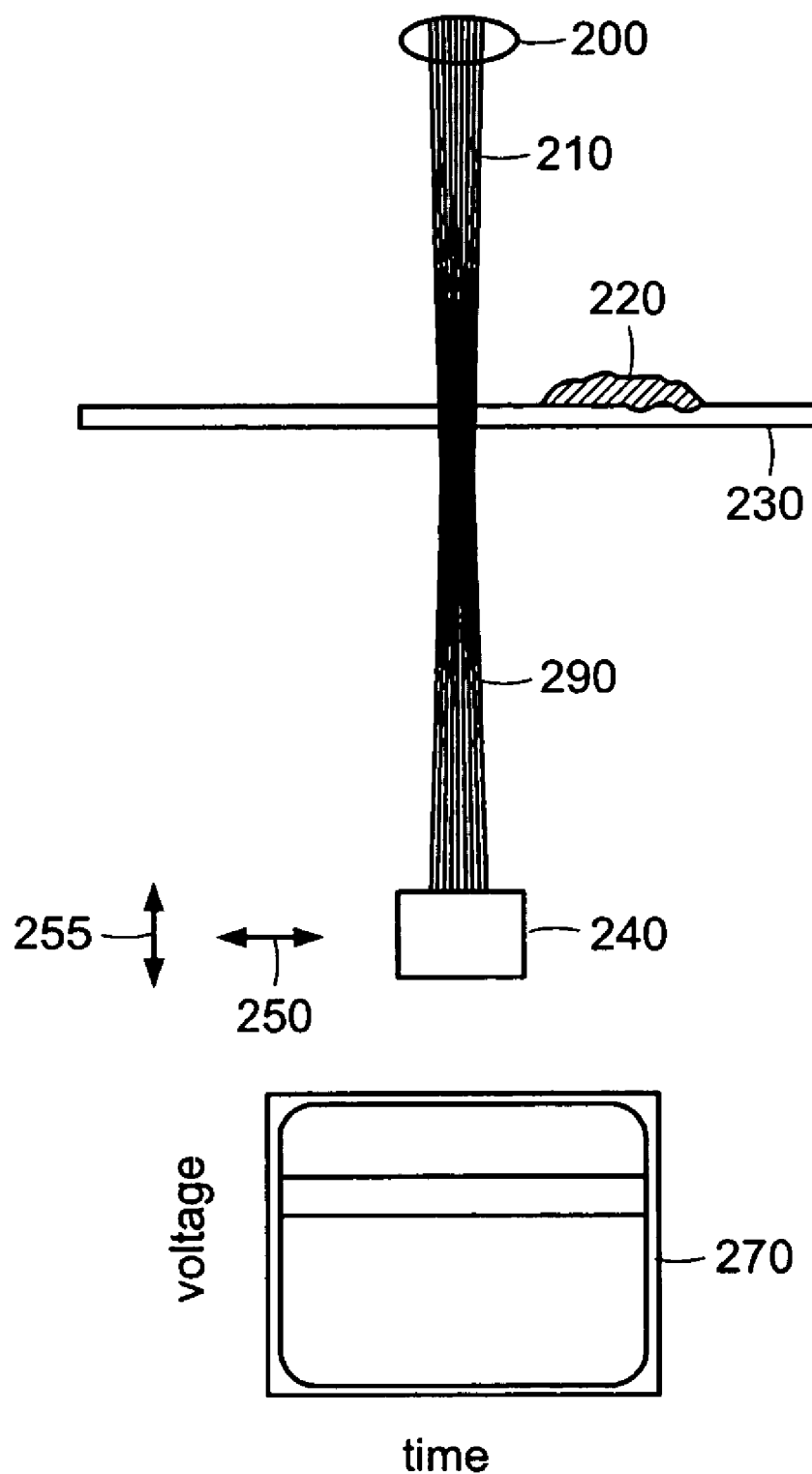
FIG. 2A depicts an embodiment of the invention used to create a contrast-field image based upon light loss when a beam of light does not impinge a sample.
Figure 2B:
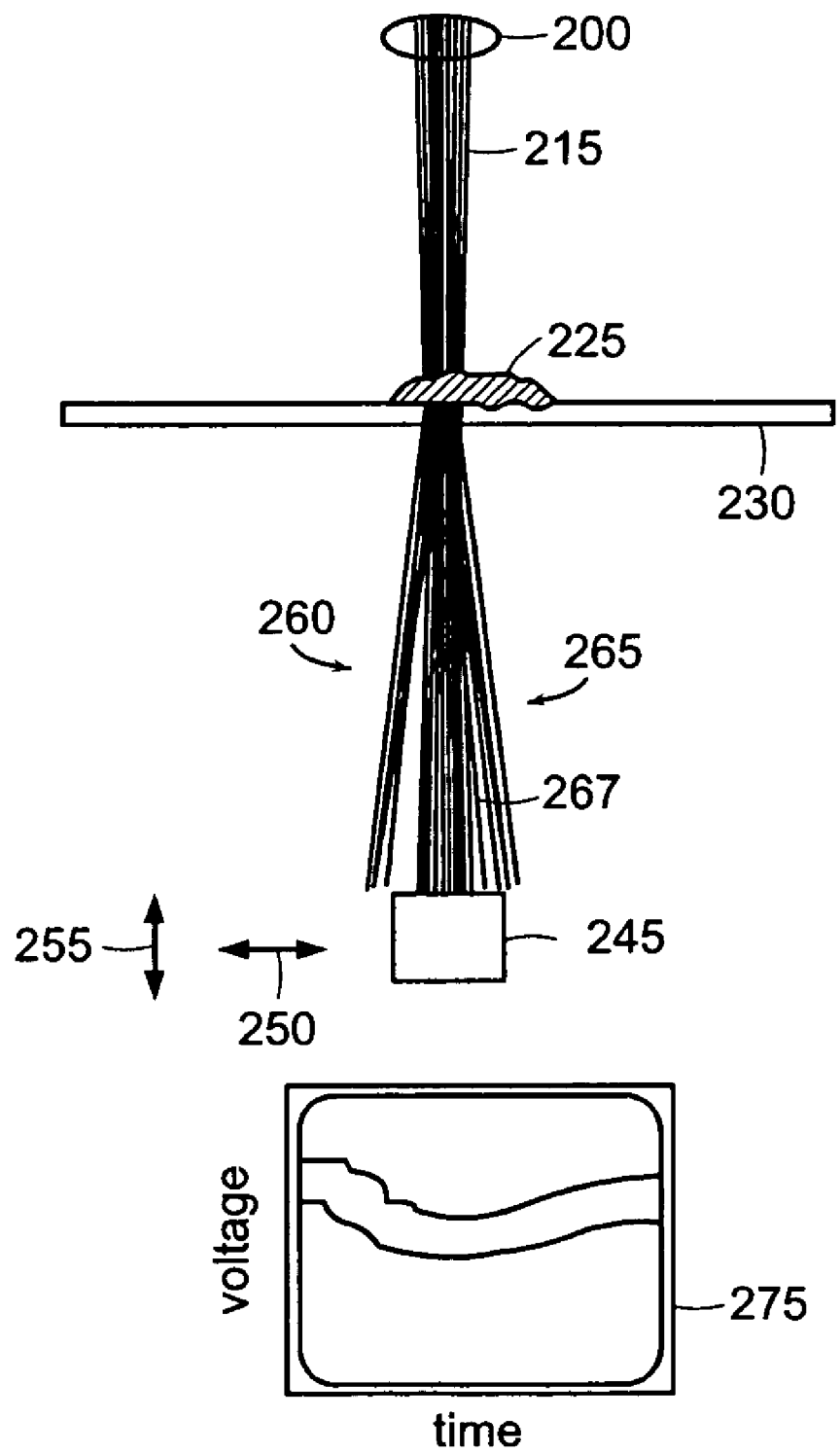
FIG. 2B depicts an embodiment of the invention used to create a contrast-field image based upon light loss when a beam of light impinges a sample.
Figure 8:
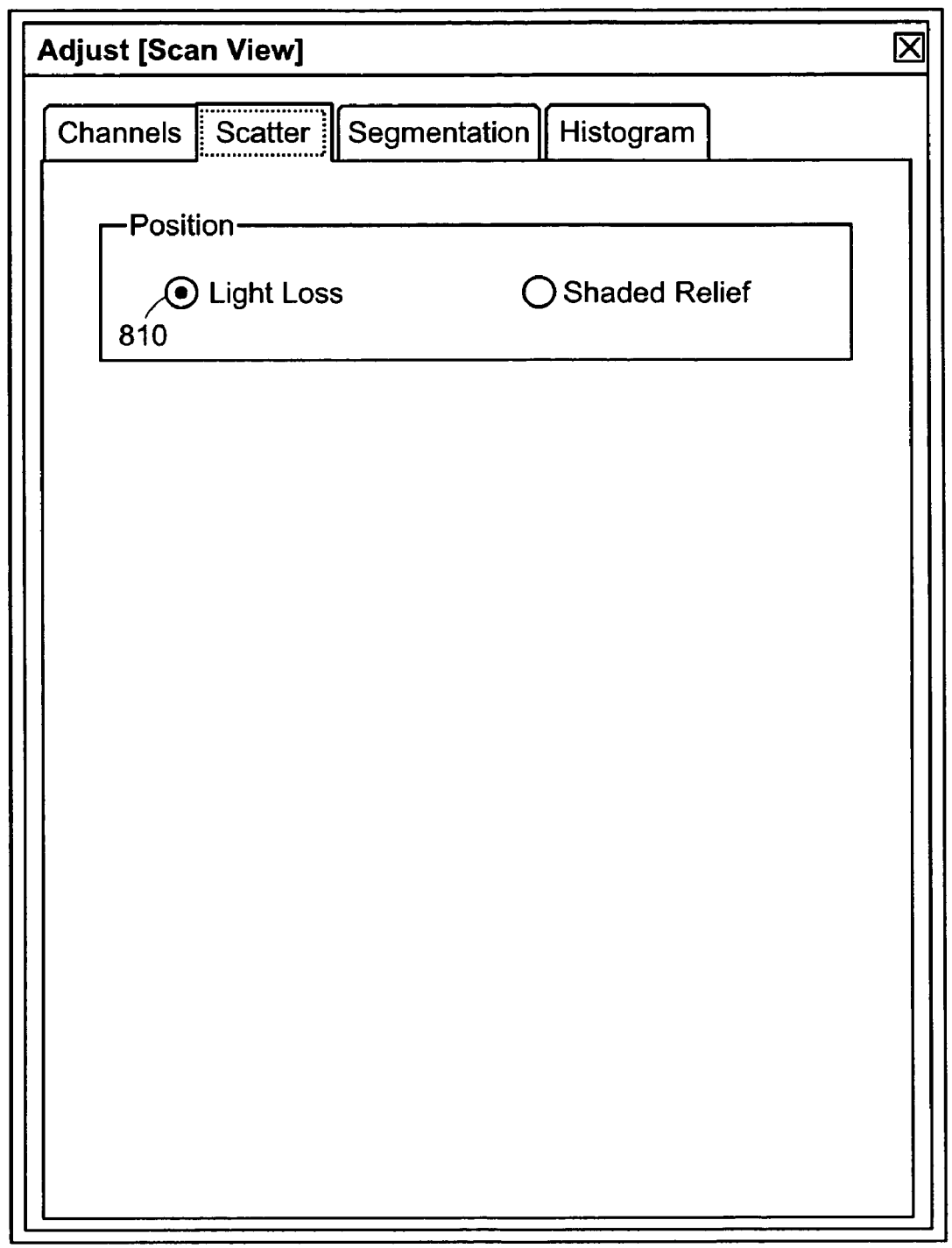
FIG. 8 depicts a graphical user interface which may be used to choose a light loss mode and view an image generated in accordance with the embodiments of FIGS. 2A-2B.

The embodiment depicted in FIGS. 2A and 2B corresponds to the light loss mode mentioned above whereby the entire transmitted laser beam impinges on the detector. FIG. 8 depicts a graphical user interface which may be used select the light loss mode and view an image generated in accordance with the embodiments of FIGS. 2A-2B. For example, a user may click on field 810 to choose the light loss mode as opposed to the shaded relief mode.

As will be explained in more detail below, in accordance with this embodiment, the detector is physically moved to a position such that its geographical center coincides with the geographical location of the unobstructed interrogating laser beam. Variations in the intensity of the signal caused by laser light absorption, refraction, scatter and conversion to fluorescence may be measured. Depending on the application, the processed light loss signal measurement arrays may be used to obtain quantitative data, such as the absorbance of light by a chromaphore. Further, the signals may be electronically inverted to obtain a signal used for identification of events of interest in a manner analogous to that described in prior art associated with laser scanning cytometry. In accordance with one embodiment of the invention, this location is fixed by calibration procedures to be described below, and there are no user adjustable settings.

In accordance with the embodiment of FIGS. 2A and 2B, a light detection device and method enables the creation of a contrast-field image of a sample (e.g., cell) without the use of a blocker bar. As shown in FIG. 2A, a light source 200 creates a beam 210 that a detector 240 is capable of detecting when the beam 210 strikes the detector 240. The embodiment may incorporate the use of LSC, as previously described. A slide 230, which may contain a sample 220, is scanned in the manner previously described. The emitted beam 210 is only attenuated substantially by the slide 230 and any contents supported by the slide 230 before the transmitted beam 290 impinges the detector 240.

The detector 240 of the embodiment is configured such that when a sample 220 is not impinged by the beam 210 the detector 240 captures (or detects) the beam 290 transmitted through the slide 230. A voltage versus time plot 270, as previously described, corresponding to the amount of light detected by the detector 240 as the slide 230 is scanned, may be created. When the beam 210 does not strike a sample 220, such a plot registers a constant voltage. As shown in FIG. 2B, when a sample 225 is impinged by a beam 215, forward scattered light 260, 265 is created. As well the remaining transmitted beam 267 is also reduced in intensity (i.e., the beam is a light loss beam) due to a number of mechanisms such as scattering, refraction, and absorption. The detector is configured to produce a signal capable of distinguishing between a transmitted beam 267 that has impinged a sample 225 and a transmitted beam 290 that has not impinged a sample 220. Such a detector configuration includes such characteristics as having a detector sensitivity capable of distinguishing the differing amounts of light captured, and sizing and positioning the detector to capture (or detect) a light loss beam while missing impingement by at least portions of forward scattered light (as depicted in FIG. 2B). Thus, as a slide 230 is scanned, a graph of voltage signal produced by the detector as a function of time 275 shows the modulation of a transmitted beam as a sample is scanned. The voltage signals may be registered with corresponding positions on the slide that are scanned to create a dark image of any sample on a slide with a bright background 280, as shown in FIG. 2C. The dark image may be inverted to create a bright image of the sample with a dark background.

The detector may be adjustably positioned in various directions 250, 255 to alter light loss detection to change the contrast of a created contrast-field image. For example, if various samples on a slide 230 are located at different depths, manipulation of the detector position may alter the contrast of the image to improve the depiction of sample details by changing the amount of negative scatter undetected by the detector.

The contrast-field image that may be created by the embodiment of the invention shown in FIGS. 2A and 2B is similar in nature to the contrast-field images of former LSC systems that utilize a blocker. The embodiment however relies on detecting light loss, while the former LSC systems create an image on the basis of captured or detected forward scattered light.

Figure 6:
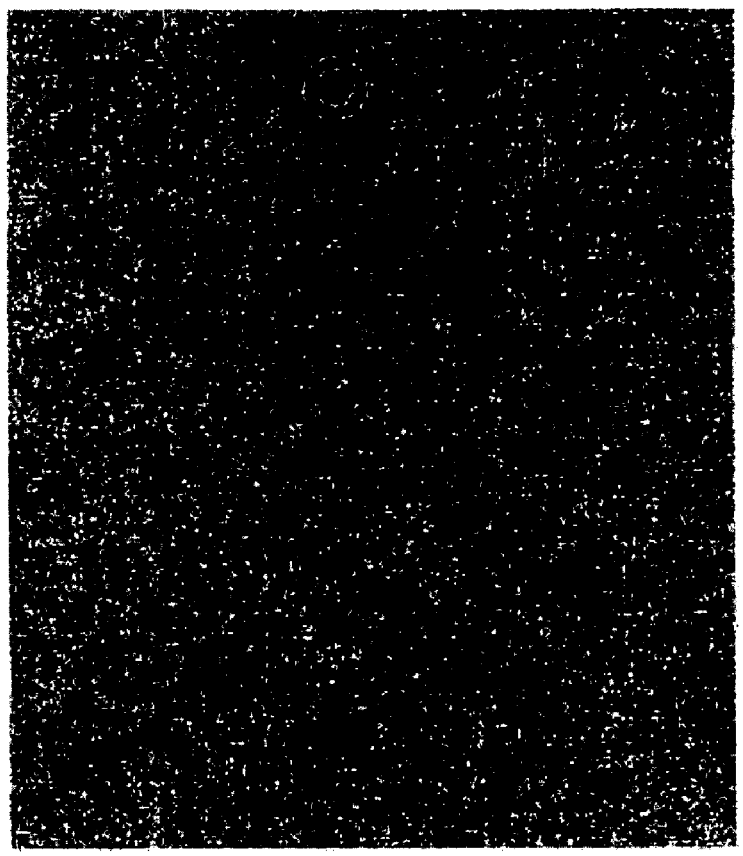
FIG. 6 depicts an visual image of calibration beads generated in accordance with the embodiment of the FIGS. 2A-2B.
Figure 7:
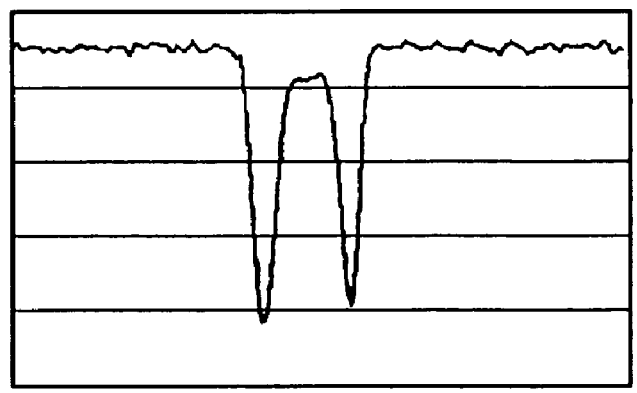
FIG. 7 depicts and graphical illustration of a pixel intensity profile through a bead of FIG. 6.

FIG. 6 depicts a demonstration of the light loss mode wherein a portion of a microscope slide containing 10 micron calibration particles was scanned. As depicted in FIG. 6 the edges of the beads exhibit the most light loss, in a relatively symmetrical manner. This is also seen in the pixel intensity profile that was obtained for a line going through a single bead depicted in FIG. 7. In accordance with FIG. 7, the X-axis displays the geographic location, and the Y-axis displays the pixel intensity.

In order to calibrate the detector, an appropriate user interface may permit an operator to determine appropriate positioning for the detector as well as providing feedback (via, for example, a waveform display indicating voltage versus time which may be employed with any laser in the system). The detector may be initially calibrated at two or more distinct positions such as: 1) when the transmitted beam is centered on the detector for light loss detection; 2) a contrast enhancement position on one edge of the detector wherein half of the transmitted beam is incident on the detector; or 3) other positions as required. Calibration for position 1 is accomplished by visually centering the detector in relation to the transmitted beam with no sample present. Calibration of position 2 is accomplished by viewing the waveform at position 1, and moving the detector position until the waveform amplitude decreases by 50% from the values at position 1. Calibrated positions may be stored a computer or processor memory for retrieval during scanning. Offsets from the calibrated positions may be defined by the operator at any time and used in the scanning of a sample. Additionally, the system may be configured with a variety of position sensing detectors to allow for determining a start (or "home") position as well as a single or multiple operational positions.

In accordance with further embodiments of the invention, the embodiments previously described may be practiced by a single device. A detector may be configured such that the detector may be alternately positioned to create a visual image or an image from the detection of light loss. The detector may be sized, oriented, and positioned optimally to maximize the flexibility of such a device to create either type of image.

The aforementioned embodiments are intended to be merely exemplary; numerous variations and modifications will be apparent to those skilled in the art. All such variations and modifications are intended to be within the scope of the present invention.

What is claimed is:

1. A method of using laser scanning cytometry system to provide a viewable image of a specimen comprising:
   positioning a detector with asymmetric exposure to a beam of light unobstructed by the specimen and without presence of a light blocker between a light source and the detector to identify a calibrated position in which a predetermined fraction of the beam of light is measured;
   exposing the specimen to at least a portion of the beam of light from the light source;
   capturing forward scattered light with the detector after the beam impinges the specimen to produce an image of the specimen; and
   offsetting the position of the detector relative to the beam of light to control the contrast of the image.

2. A method according to claim 1, wherein offsetting the position of the detector is determined by the acts of:
   impinging at least a portion of light from the light source onto a portion of a movable sample support, wherein the at least a portion of beam of light does not impinge the specimen; and
   establishing a calibration point by measuring light from the at least a portion of the beam after the at least a portion of the beam impinges the movable sample support.

3. A method according to claim 2, wherein establishing the calibration point includes moving the detector to a position such that the detector detect a signal having a maximum intensity and moving the detector to a position such that the detector detects a signal having the predetermined fraction of the maximum intensity.

4. A method for producing an image of a specimen comprising:
   producing a beam of light from a laser light source;
   positioning a detector with asymmetric exposure to the beam of light unobstructed by the specimen and without presence of a light blocker between the light source and the detector to identify a calibration position in which a predetermined fraction of the beam of light from the light source is measured;
   adjusting the position of the detector such that only a portion of the beam of light from the light source is detected to produce a signal of a first intensity;
   adjusting the position of the detector such that light scattered by the specimen is detected to produce a signal of a second intensity; and
   using the signals to form a visual image of the specimen.

5. A method according to claim 4, wherein adjusting the position of the detector such that light scattered by the specimen is detected includes adjusting the position of the detector such that forward scattered light is detected.

6. A method according to claim 4, further comprising adjusting the position of the detector such that light refracted by the specimen is detected and producing a signal of a third intensity.

7. A method according to claim 4, further comprising adjusting the position of the detector such that light converted to fluorescence is detected and producing a signal of a fourth intensity.

8. A method according to claim 4, wherein producing a beam of light includes producing a beam of monochromatic light.

9. A method according to claim 4, wherein producing a beam of light includes Producing a beam of light using laser scanning cytometry.

10. A system for creating a contrast-field image of a sample, the system comprising:
   a source of a beam of light;
   a movable sample support for supporting a sample, the movable sample support and the beam of light being moved relative to one another such that a desired portion of the sample support can be scanned by the beam;
   a movable detector, the detector being offsettably movable with respect to the beam of light, so as to assume a calibrated offset position relative to the beam of light, said calibrated offset position defined as a position at which a predetermined fraction of the light from the light source is detected by the detector without presence of any light blocker between the light source and the detector.

11. The system of claim 10 further comprising a computer memory for storing the calibrated offset position of the movable detector relative to the beam of light.

12. A method for producing an image of a specimen comprising:
    producing a beam of light;
    positioning a detector at a calibrated offset position with asymmetric exposure to the beam of light, the calibrated offset position defined as a position at which a predetermined fraction of the light from the beam is detected by the detector without presence of any light blocker between the beam and the detector;
    producing a signal at the detector responsive to light detected by the detector; and
    using the signal to form a visual image of the specimen.

13. The method of claim 12, wherein producing a signal is responsive to light forward scattered by the specimen.

14. The method of claim 12, wherein producing a signal is responsive to light refracted by the specimen.

15. The method of claim 12, wherein producing a signal is responsive to light converted to fluorescence.

16. The method of claim 12, wherein producing a beam of light comprises producing a laser beam.

17. The method of claim 12, further comprising establishing the calibrated offset position by moving the detector to a position such that the detector detects a signal having a maximum intensity and moving the detector to a position such that the detector detects a signal having the predetermined fraction of the maximum intensity.

18. The method of claim 17, further comprising storing the calibrated offset position in memory for repeatably returning the detector to the calibrated offset position.

* * * * *

UNITED STATES PATENT AND TRADEMARK OFFICE
CERTIFICATE OF CORRECTION

| | | |
|---|---|---|
| PATENT NO. | : 7,706,590 B2 | Page 1 of 1 |
| APPLICATION NO. | : 11/040183 | |
| DATED | : April 27, 2010 | |
| INVENTOR(S) | : Edgar A. Luther | |

It is certified that error appears in the above-identified patent and that said Letters Patent is hereby corrected as shown below:

In Col. 8, line 8 claim 2
replace "portion of light"
with "portion of the beam of light"

In Col. 8, line 17 claim 3
replace "detect"
with "detects"

In Col. 8, line 53 claim 9
replace "Producing"
with "producing"

Signed and Sealed this
Twenty-sixth Day of April, 2011

David J. Kappos
*Director of the United States Patent and Trademark Office*